(12) United States Patent
Baldo et al.

(10) Patent No.: US 6,391,287 B1
(45) Date of Patent: May 21, 2002

(54) COMPOSITION CONTAINING AT LEAST ONE BICYCLIC AROMATIC COMPOUND AND AT LEAST ONE LIPOPHILIC SUNSCREEN, AND USES THEREOF

(75) Inventors: Francine Baldo, Sceaux; Carole Guiramand, Linas, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/567,046

(22) Filed: May 8, 2000

(30) Foreign Application Priority Data

May 6, 1999 (FR) .............................. 99 05784

(51) Int. Cl.[7] .............................. A61K 7/42; A61K 7/44; A61K 7/00
(52) U.S. Cl. .......................... 424/59; 424/60; 424/400; 424/401; 514/859
(58) Field of Search .................... 424/59, 60, 400, 424/401

(56) References Cited

U.S. PATENT DOCUMENTS 5,672,710 A 9/1997 Beard et al. ............... 548/188
5,763,487 A 6/1998 Bernardon .................. 514/569

FOREIGN PATENT DOCUMENTS

FR 2 761 600 10/1998

*Primary Examiner*—Shelley A. Dodson
(74) *Attorney, Agent, or Firm*—Oblon, Spivak, McClelland, Maier & Neustadt, P.C.

(57) ABSTRACT

A composition containing at least one lipophilic sunscreen and at least one bicyclic aromatic compound represented by formula (I):

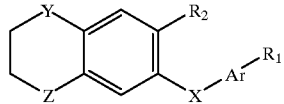

or a salt or chiral analogue of such a compound, where the structural variables $R_1$, Ar, X, $R_2$ Y and X are defined herein, and at least one lipophilic sunscreen.

21 Claims, No Drawings

COMPOSITION CONTAINING AT LEAST ONE BICYCLIC AROMATIC COMPOUND AND AT LEAST ONE LIPOPHILIC SUNSCREEN, AND USES THEREOF

BACKGROUND OF THE INVENTION

1. Field of the Invention

The present invention relates to a composition containing at least one bicyclic aromatic compound and at least one lipophilic sunscreen, to uses of the composition, and to a process for dissolving the compound with at least one lipophilic sunscreen.

2. Discussion of the Background

Bicyclic aromatic compounds with retinoid-type activity, which are useful in particular in preventing or treating various keratinization disorders, are described in EP 679 630. These compounds are cosmetic active agents of choice, in particular for repairing or combating chronological or actinic ageing of the skin, for example such as in anti-wrinkle products.

However, it has been observed that these compounds are difficult to dissolve in cosmetic compositions. Thus, these active agents have a tendency to recrystallize or to be degraded. This leads to a more or less pronounced loss of efficacy of the compositions containing them, depending on the degree of recrystallization and/or of degradation, which runs counter to the desired objective. In addition, this recrystallization or degradation can modify the overall stability of these compositions, as well as their appearance, which dissuades consumers from using these products.

There is thus a need to dissolve these compounds in a physiologically acceptable solubilizing agent.

It is also known from WO 97/31620 to use lipophilic screening agents, such as octocrylene and octyl methoxycinnamate, together with compounds with retinoid-type activity. These lipophilic screening agents are intended to modulate the irritation induced by the retinoids by delaying and/or modulating their release.

The retinoids to which reference is made in WO 97/31620 are retinol, retinal and retinoic acid, are irritant compounds. On the other hand, the bicyclic aromatic compounds mentioned above, which have retinoid-type activity similar to that of retinol or retinoic acid, have the advantage over the retinoids given as examples in WO 97/31620 of not being irritating.

Consequently, it was not obvious to a person skilled in the art that the combination of the bicyclic aromatic compounds described below with lipophilic sunscreens would be of any value.

SUMMARY OF THE INVENTION

The present Inventors have now discovered, surprisingly, that lipophilic sunscreens make it possible to dissolve the bicyclic aromatic compounds discussed above. The present invention is based on this discovery.

Thus, the present invention provides a composition comprising at least one bicyclic aromatic compound and at least one lipophilic sunscreen.

The present invention also provides a process for dissolving a bicyclic aromatic compound by mixing the bicyclic compound with at least one lipophilic sunscreen. The mixing can be carried out under a wide variety of conditions, e.g., cold conditions, at room temperature, or under warm conditions, for example at 80° C., generally with stirring.

A more complete appreciation of the invention and many of the attendant advantages thereof will be readily obtained as the same becomes better understood by reference to the following detailed description.

DETAILED DESCRIPTION OF THE INVENTION

The bicyclic aromatic compounds according to the invention have, specifically, the general formula (I) below:

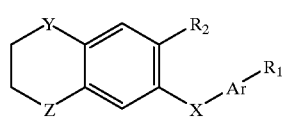

(I)

where $R_1$ represents a hydrogen atom, a radical —$CH_3$, a radical —$CH_2$—O—$R_3$, a radical —$CH_2$—O—CO—$R_4$, a radical —O—$R_5$, a radical —O—$(CH_2)_m$—$(CO)_n$—$R_6$, a radical —CO—O—$R_8$ or a radical —$S(O)_p$—$R_9$, the values m, n and p and the various radicals $R_3$ to $R_9$ having the meaning described below, $R_2$ represents a hydrogen atom or a halogen atom, a lower alkyl radical, an —$NO_2$ radical, a radical —O—$COR_4$, a radical —$OR_9$ or a radical:

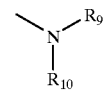

the radicals $R_4$, $R_9$ and $R_{10}$ having the meaning described below, Ar represents a radical chosen from the radicals of formulae (a)-(e) below:

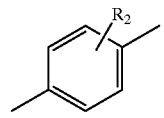

(a)

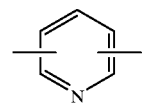

(b)

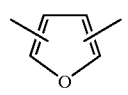

(c)

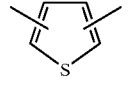

(d)

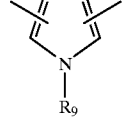

(e)

in which $R_2$ is described above and $R_9$ has the meaning described below, X represents —O—, —$S(O)_t$— or a radical —NR$_9$—, the value t and the radical R$_9$ having the meaning described below, Y and Z represent —O—, —S(O)$_t$— or a radical —CR$_{11}$R$_{12}$, the value t and the radicals R$_{11}$ and R$_{12}$ having the meaning described below, it being understood that, in all of the text hereinabove:

m is an integer equal to 1, 2 or 3, n is an integer equal to 0 or 1, p is an integer equal to 0, 1, 2 or 3 and t is an integer equal to 0, 1 or 2, R$_3$, R$_5$, R$_9$, R$_{10}$, R$_{11}$, and R$_{12}$ represent, independently of each other, a hydrogen atom or a lower alkyl radical, R$_4$ represents a lower alkyl radical, R$_6$ represents a lower alkyl radical or a heterocycle, R$_7$ represents a hydrogen atom, a lower alkyl radical or a radical:

in which R' and R", which may be identical or different, represent a hydrogen atom, a lower alkyl radical, a mono- or polyhydroxyalkyl radical, an optionally substituted aryl radical or an amino acid or peptide or sugar residue, or alternatively, taken together, form a heterocycle, R$_8$ represents a hydrogen atom, a linear or branched alkyl radical containing from 1 to 20 carbon atoms, an alkenyl radical, a mono- or polyhydroxyalkyl radical, an optionally substituted aryl or aralkyl radical, a sugar residue or an amino acid or peptide residue, Y and Z cannot simultaneously represent an oxygen atom or a radical —S(O)$_t$—.

The invention is also directed towards the salts of the compounds of formula (I) above when the radical R$_1$ represents a carboxylic acid function or a sulfonic acid function or bears an amine function, or alternatively when the radical R$_2$ represents an amine function, as well as the chiral analogues of the said compounds. When the compounds according to the invention are in the form of salts, they are preferably salts of an alkali metal or alkaline-earth metal, or alternatively of zinc or of an organic amine.

According to the present invention, the term "lower alkyl radical" refers to a radical containing from 1 to 6 carbon atoms, preferably methyl, ethyl, isopropyl, butyl, tert-butyl and hexyl radicals.

The term "linear or branched alkyl radical containing from 1 to 20 carbon atoms" refers to methyl, ethyl, propyl, 2-ethylhexyl, octyl, dodecyl, hexadecyl and oxadecyl radicals.

The term "monohydroxyalkyl radical" refers to radical preferably containing 2 or 3 carbon atoms, in particular a 2-hydroxyethyl, 2-hydroxypropyl or 3-hydroxypropyl radical.

The term "polyhydroxyalkyl radical" refers to radical preferably containing from 3 to 6 carbon atoms and from 2 to 5 hydroxyl groups, such as 2,3-dihydroxypropyl, 2,3,4-trihydroxybutyl and 2,3,4,5-tetrahydroxypentyl radicals or a pentaerythritol residue.

The term "aryl radical" preferably refers to a phenyl radical optionally substituted with at least one halogen atom, a hydroxyl or a nitro function.

The term "aralkyl radical" preferably refers to a benzyl or phenethyl radical optionally substituted with at least one halogen atom, a hydroxyl or a nitro function.

The term "alkenyl radical" refers to a radical preferably containing from 2 to 5 carbon atoms and containing one or more ethylenic unsaturations, such as, more particularly, an allyl radical.

The term "sugar residue" refers to a residue derived in particular from glucose, galactose or mannose, or alternatively from glucuronic acid.

The term "amino acid residue" in particular refers to a residue derived from lysine, glycine or aspartic acid, and the expression "peptide residue" more particularly means a dipeptide or tripeptide residue resulting from the combination of amino acids.

The term "heterocycle" preferably means a piperidino, morpholino, pyrrolidino or piperazino radical, optionally substituted in position 4 with a C$_1$–C$_6$ alkyl or mono- or polyhydroxyalkyl radical as defined above.

When the radical R$_2$ represents a halogen atom, it is preferably a fluorine, chlorine or bromine atom.

In the present invention, the compounds of formula (I) which are more particularly preferred are those for which at least one, and preferably all, of the conditions below are satisfied:

R$_1$ is a radical —CO—R$_7$

R$_2$ is a lower alkyl radical or a radical —OR$_9$

Ar represents a radical of formula (a)

and X represents —O—, —S— or —NR$_9$—.

Specific examples of compounds of formula (I) include:

4-(5,6,7,8-Tetrahydro-5,5,8,8-tetramethyl-2-naphthyloxy)benzoic acid, 4-(5,6,7,8-Tetrahydro-5,5,8,8-tetramethyl-2-naphthylthio)benzoic acid, 4-(5,6,7,8-Tetrahydro-5,5,8,8-tetramethyl-2-naphthylsulfinyl)benzoic acid, 4-(5,6,7,8-Tetrahydro-5,5,8,8-tetramethyl-2-naphthylsulfonyl)benzoic acid, 4-(5,6,7,8-Tetrahydro-5,5,8,8-tetramethyl-2-naphthylamino)benzoic acid, 5-(5,6,7,8-Tetrahydro-5,5,8,8-tetramethyl-2-naphthylthio)-2-thiophenecarboxylic acid, 4-(3,5,5,8,8-Pentamethyl-5,6,7,8-tetrahydro-2-naphthyloxy)benzoic acid, 4-(3,5,5,8,8-Pentamethyl-5,6,7,8-tetrahydro-2-naphthylthio)benzoic acid, 4-(3-Ethyl-5,5,8,8-tetramethyl-5,6,7,8-tetrahydro-2-naphthyloxy)benzoic acid, 4-(3-Isopropyl-5,5,8,8-tetramethyl-5,6,7,8-tetrahydro-2-naphthyloxy)benzoic acid, 4-(5,6,7,8-tetrahydro-5,5,8,8-tetramethyl-2-naphthyloxy)acetophenone, 4-(5,6,7,8-tetrahydro-5,5,8,8-tetramethyl-2-naphthyloxy)benzaldehyde, 4-(3-Bromo-5,6,7,8-tetrahydro-5,5,8,8-tetramethyl-2-naphthyloxy)benzoic acid, 3-Methyl-4-(5,6,7,8-tetrahydro-5,5,8,8-tetramethyl-2-naphthylthio)benzoic acid, 3-Methyl-4-(3,5,5,8,8-pentamethyl-5,6,7,8-tetrahydro-2-naphthylthio)benzoic acid, 3-Methyl-4-(3-ethyl-5,6,7,8-tetrahydro-5,5,8,8-tetramethyl-2-naphthyloxy)benzoic acid, 6-(3,5,5,8,8-Pentamethyl-5,6,7,8-tetrahydro-2-naphthylthio)nicotinic acid, 2-Hydroxy-4-(3,5,5,8,8-pentamethyl-5,6,7,8-tetrahydro-2-naphthylthio)benzoic acid, 2-Chloro-4-(3,5,5,8,8-pentamethyl-5,6,7,8-tetrahydro-2-naphthylthio)benzoic acid, 4-(3-Ethyl-5,6,7,8-tetrahydro-5,5,8,8-tetramethyl-2-naphthylthio)benzoic acid, 4-(3-Isopropyl-5,6,7,8-tetrahydro-5,5,8,8-tetramethyl-2-naphthylthio)benzoic acid,
4-(3-n-Propyl-5,6,7,8-tetrahydro-5,5,8,8-tetramethyl-2-naphthylthio)benzoic acid,
4-(3,5,5,8,8-Pentamethyl-5,6,7,8-tetrahydro-2-naphthylthio)benzenemethanol,
4-(3,5,5,8,8-Pentamethyl-5,6,7,8-tetrahydro-2-naphthylthio)benzaldehyde,
N-Ethyl-4-(3,5,5,8,8-pentamethyl-5,6,7,8-tetrahydro-2-naphthylthio)benzamide, and
N-4-Hydroxyphenyl-4-(3,5,5,8,8-pentamethyl-5,6,7,8-tetrahydro-2-naphthylthio)benzamide.

It is particularly preferred to use 4-(3,5,5,8,8-pentamethyl-5,6,7,8-tetrahydro-2-naphthylthio)benzoic acid in the composition according to the invention.

The inventive composition also contains at least one lipophilic sunscreen as solubilizing agent for the above bicyclic aromatic compounds.

As lipophilic sunscreens which are suitable for use in the present invention, mention may be made in particular of: p-aminobenzoic acid derivatives, such as the esters, salts or amides of p-aminobenzoic acid; salicylic acid derivatives, such as the esters or salts of salicylic acid; benzophenone derivatives; dibenzoylmethane derivatives; diphenylacrylate derivatives; benzofuran derivatives; polymeric UV screening agents containing one or more organosilicon residues; cinnamic acid esters; camphor derivatives; trianilino-s-triazine derivatives; phenylbenzimidazolesulfonic acid and its salts; urocanic acid or its ethyl ester; benzotriazoles; hydroxyphenyltriazine derivatives; bis(resorcinol) dialkylaminotriazines; and mixtures thereof.

The lipophilic sunscreen according to the invention is preferably chosen from: octyl salicylate; 3-benzophenone; butylmethoxydibenzoylmethane; octocrylene; octyl methoxycinnamate and the compound of formula (II) below, or 2-(2H-benzotriazol-2-yl)-4-methyl-6-[2-methyl-3-[ 1,3,3,3-tetramethyl-1 -[(trimethylsilyl)oxy]disiloxanyl]-propynyl] phenol, described in EP-A-0 392 883:

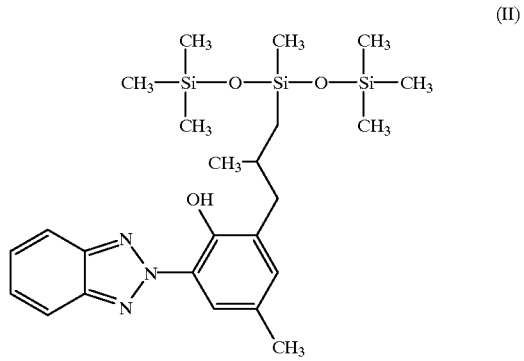

(II)

The compound of formula (I) is present in the composition according to the invention in an amount which is effective to obtain the desired effect, for example between 0.0001% and 10% by weight, preferably between 0.001 and 5% by weight, more preferably between 0.01 and 1% by weight, relative to the composition as a whole. In addition, the lipophilic sunscreen is present in the composition according to the invention in an amount which is sufficient to dissolve the compound of formula (I) and which is effective to give the composition, alone or in combination with hydrophilic screening agents, the desired sun protection factor (SPF). The amount of lipophilic screening agent is thus preferably between 0.001% and 30% by weight relative to the composition as a whole.

The composition according to the invention can be in any pharmaceutical form normally used for topical application to the skin, in particular in the form of an aqueous, aqueous-alcoholic or oily solution, an oil-in-water or water-in-oil or multiple emulsion, a silicone emulsion, a microemulsion or nanoemulsion, an aqueous or oily gel, an anhydrous liquid, pasty or solid product, a dispersion of oil in an aqueous phase in the presence of spherules, it being possible for these spherules to be polymeric nanoparticles such as nanospheres and nanocapsules or, better still, lipid vesicles of ionic and/or nonionic type.

This composition can be more or less fluid and can have the appearance of a white or colored cream, an ointment, a milk, a lotion, a serum, a paste, a mousse or a gel. It can optionally be applied to the skin in the form of an aerosol. It can also be in solid form and, for example, in the form of a stick. It can be used as a care product and/or as a make-up product for the skin, or as a hair product, for example as a shampoo or conditioner.

In a known manner, the composition of the invention can also contain adjuvants that are common in cosmetics and dermatology, such as hydrophilic or lipophilic gelling agents, hydrophilic or lipophilic active agents, preserving agents, antioxidants, solvents, fragrances, fillers (such as starch, talc or Nylon), pigments, hydrophilic screening agents, odour absorbers and dyestuffs. The amounts of these various adjuvants are those conventionally used in the fields considered, and, for example, from 0.01 to 20% relative to the total weight of the composition. Depending on their nature, these adjuvants can be introduced into the fatty phase, into the aqueous phase, into the lipid vesicles and/or into the nanoparticles. These adjuvants, as well as their concentrations, should be such that they do not harm the advantageous properties of the bicyclic aromatic compound according to the invention.

When the composition according to the invention is an emulsion, the proportion of the fatty phase can range from 5 to 80% by weight, and preferably from 5 to 50% by weight, relative to the total weight of the composition. The fatty substances, the emulsifiers and the co-emulsifiers used in the composition in emulsion form are chosen from those conventionally used in the field considered. The emulsifier and co-emulsifier are preferably present in the composition in a proportion ranging from 0.3 to 30% by weight, and preferably from 0.5 to 20% by weight, relative to the total weight of the composition.

As fatty substances which can be used in the invention, mention may be made of oils and in particular mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols such as cetyl alcohol, fatty acids, waxes and gums, and in particular silicone gums, can also be used.

It is particularly preferable to use as fatty substances at least one Guerbet alcohol or 2-alkyl-1-alkanol, or an ester of such an alcohol, which act as co-solubilizing agents for the bicyclic aromatic compounds. Examples of 2-alkyl-1-alkanols which are suitable for use in the present invention are, in particular: butyloctanol, hexyldecanol, octyldecanol, isostearyl alcohol, octyldodecanol, decyltetradecanol, undecylpentadecanol, dodecylhexadecanol, tetradecyloctadecanol, hexyldecyloctadecanol, tetradecyleicosanol and cetylarachidol. As esters of the said alcohols, mention may be made of: octyldodecyl octanoate; hexyldecyl caprylate; hexyldecyl laurate; hexyldecyl palmitate; hexyldecyl stearate; and octyldodecyl meadowfoamate, which is an ester of octyldodecanol and of fatty acids derived from the germ oil of *Limnanthes alba*.

As emulsifiers and co-emulsifiers which can be used in the invention, it is particularly advantageous to use fatty acid esters of polyols, such as PEG-100 stearate, PEG-50 stearate and PEG-40 stearate; glyceryl stearate, sorbitan tristearate, the oxyethylenated sorbitan stearates available under the tradenames Tween® 20 or Tween® 60, for example; and mixtures thereof.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays and, as lipophilic gelling agents, mention may be made of modified clays such as bentones, metal salts of fatty acids and hydrophobic silica.

Active agents which can be used in particular are depigmenting agents, emollients, moisturizers, anti-seborrhoeic agents, anti-acne agents, agents for promoting regrowth of the hair, keratolytic and/or desquamating agents, anti-irritant agents, calmants and mixtures thereof. Advantageously, in the composition according to the invention, the bicyclic aromatic compounds defined above are used in combination with other compounds which have retinoid-type activity, with free-radical scavengers, or with α-hydroxy or α-keto acids or derivatives thereof. The term "free-radical scavenger" refers to, for example, α-tocopherol, superoxide dismutase, ubiquinol or certain metal-chelating agents. The term "α-hydroxy or α-keto acids or derivatives thereof" refers to, for example, lactic, malic, citric, glycolic, mandelic, tartaric or glyceric acids or the salts, amides or esters thereof.

In the event of incompatibility, the active agents indicated above can be incorporated into spherules, in particular ionic or nonionic vesicles and/or nanoparticles (nanocapsules and/or nanospheres), so as to isolate them from each other in the composition.

The composition according to the invention in particular finds an application in body and hair hygiene, and in particular to care for acne-prone skin or squamous skin, to combat the greasy appearance of the skin or the hair, to combat hair loss, in protecting against the harmful aspects of sunlight or to prevent and/or combat actinic or chronological ageing.

The present invention thus also relates to the use of the composition mentioned above for the cosmetic treatment of the skin, in particular against acne and/or chronological or actinic ageing. The invention also relates to the use of this composition for the cosmetic treatment of the scalp, in particular to combat the greasy appearance of the hair and hair loss.

The present invention also relates to the use of the composition mentioned above to manufacture a preparation intended to combat acne and/or chronological or actinic ageing of the skin. The invention also relates to the use of the composition mentioned above to manufacture a preparation intended to combat the greasy appearance of the hair and hair loss.

In each of these embodiments, the composition according to the invention and/or the preparation obtained therefrom comprises an effective amount of bicyclic aromatic compound in a physiologically acceptable medium.

EXAMPLES

Having generally described this invention, a further understanding can be obtained by reference to certain specific examples which are provided herein for purposes of illustration only and are not intended to be limiting unless otherwise specified. In the following Examples, the amounts indicated are percentages by weight, except where as specified otherwise.

Example 1

The oil-in-water emulsion having the composition below was prepared:

| Phase A | |
|---|---|
| Hydrogenated polyisobutene | 20% |
| Octocrylene | 10% |
| Cetyl alcohol | 2.6% |
| PEG-100 stearate | 1.05% |
| Glyceryl stearate | 1.05% |
| Oxyethylenated (20 EO) sorbitan stearate | 0.9% |
| Bicyclic aromatic compound A* | 0.1% |
| Phase B | |
| Glycerol | |
| Preserving agents | 0.46% |
| Carbomer | 0.4% |
| Xanthan gum | 0.1% |
| Water | 55.04% |
| Phase C | |
| Triethanolamine | 0.3% |
| Water | 5% |

*A: 4-(3,5,5,8,8-Pentamethyl-5,6,7,8-tetrahydro-2-naphthylthio)benzoic acid

The constituents of phase A were mixed together and the whole was then heated at 75–80° C. for one hour. The gelling agents (xanthan gum and carbomer) were dispersed in the rest of phase B with stirring, and the whole was then heated at 75–80° C. for one hour. Phase A was then introduced into phase B with stirring over two minutes at 75–85° C. Phase C was then added to the mixture of phases A and B with stirring, after stopping the heating. Finally, the emulsion obtained was then left to cool to 25° C.

No formation of crystals was observed at the time of preparation of the emulsion, or after 24 hours at 25° C. (room temperature). It may thus be considered that the composition is stable for these periods of time, at the temperatures indicated.

Example 2

The same composition as that described in Example 1 was prepared, except that the amount of hydrogenated polyisobutene was lowered to 12% and 8% of hexyldecanol was added.

Macroscopic and microscopic analysis of the emulsion obtained shows that it is stable after storage for two months at 4° C., 25° C. (room temperature) and 45° C. In particular, no recrystallization of compound A is observed after this period of time. In addition, the stability of compound A, as determined by HPLC, is not affected.

Example 3

The same composition as that described in Example 1 was prepared, except that the octocrylene was replaced with 7.5% by weight of octyl methoxycinnamate, the amount of water in phase B being adjusted accordingly.

The same solubility results for compound A in this composition as in that of Example 1 are obtained.

Example 4

The same composition as that described in Example 3 was prepared, except that the amount of hydrogenated polyisobutene was lowered to 12% and 8% of hexyldecanol was added.

Macroscopic and microscopic analysis of the emulsion obtained shows that it is stable after storage for two months at 4° C., 25° C. (room temperature) and 45° C. In particular, no recrystallization of compound A is observed after this period of time. In addition, the stability of compound A, as determined by HPLC, is not affected.

Example 5

The same composition as that described in Example 1 was prepared, except that the octocrylene was replaced with 2% by weight of a benzotriazole silicone, 2-(2H-benzotriazol-2-yl)-4-methyl-6-[2-methyl-3-[1,3,3,3-tetramethyl-1-[(trimethylsilyl)oxy]di-siloxanyl]propynyl]phenol, the amount of water in phase B being adjusted accordingly.

The same results in terms of solubility of compound A at 24 hours as in Example 1 are obtained.

Example 6

The same composition as that described in Example 5 was prepared, except that the amount of hydrogenated polyisobutene was lowered to 12% and 8% of hexyldecanol was added.

Macroscopic and microscopic analysis of the emulsion obtained shows that it is stable after storage for two months at 25° C. (room temperature) and 45° C. In particular, no recrystallization of compound A is observed after this period of time, at the temperatures indicated. In addition, the stability of compound A, as determined by HPLC, is not affected.

Example 7

The same composition as that described in Example 1 was prepared, except that the amount of octocrylene was reduced to 4% and that 1.5% by weight of butylmethoxydibenzoylmethane and 0.3% by weight of a sequestering agent, the pentasodium salt of ethylenediaminetetramethylenephosphonic acid (at a concentration of 33% in water), were also added to the composition.

The same results in terms of solubility of compound A at 24 hours as in Example 1 are obtained.

Example 8

The same composition as that described in Example 7 was prepared, except that the amount of hydrogenated polyisobutene was lowered to 12% and 8% of hexyldecanol was added.

Macroscopic and microscopic analysis of the emulsion obtained shows that it is stable after storage for two months at 25° C. (room temperature) and 45° C., although it has a slightly yellow appearance. In particular, no recrystallization of compound A is observed after this period of time, at the temperatures indicated. In addition, the stability of compound A, as determined by HPLC, is not affected.

Example 9
(comparative)

The same composition as that described in Example 1 was prepared, except that the octocrylene was replaced with 4.5% by weight of 3,3'-terephthalylidene-10,10'-camphorsulfonic acid at a concentration of 33% in water, which is a hydrophilic sunscreen described in particular in French patent No. 82 10425 in the name of the Applicant. The triethanolamine content was also raised to 1.15% by weight.

It is found that this hydrophilic screening agent does not allow compound A to be dissolved, even at 80° C. with magnetic stirring. Crystals are visible as soon as the emulsion is formed and at 24 hours.

Example 10
(comparative)

The same composition as that described in Example 1 was prepared, except that the octocrylene was replaced with 2.5% by weight of 2-phenylbenzimidazole-5-sulfonic acid, which is a hydrophilic sunscreen sold by the company Merck under the trade name Eusolex 232. The triethanolamine content was also raised to 2.4% by weight.

It is found that this hydrophilic screening agent does not make it possible to dissolve compound A, even at 80° C. with magnetic stirring. Crystals are visible as soon as the emulsion is formed and at 24 hours.

It emerges from the text hereinabove that, unlike hydrophilic screening agents, lipophilic screening agents allow good solubilization of the bicyclic aromatic compound according to the invention. The solubilization of this compound can also be improved, without affecting its stability, by adding a Guerbet alcohol such as hexyldecanol.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-05784, filed on May 6, 1999, and incorporated herein by reference in its entirety.

What is claimed is:

1. A composition, comprising:

at least one lipophilic sunscreen; and at least one bicyclic aromatic compound represented by formula (I):

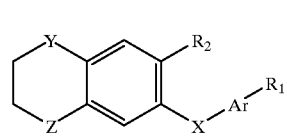

(I)

wherein $R_1$ represents a hydrogen atom, a radical —$CH_3$, a radical —$CH_2$—O—$R_3$, a radical —$CH_2$—O—CO—$R_4$, a radical —O—$R_5$, a radical —O—$(CH_2)_m$—$(CO)_n$—$R_6$, a radical —CO—$R_7$, a radical —CO—O—$R_8$ or a radical —$S(O)_p$—$R_9$, $R_2$ represents a hydrogen atom or a halogen atom, a lower alkyl radical, an —$NO_2$ radical, a radical —O—$COR_4$, a radical —$OR_9$ or a radical

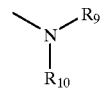

Ar represents a radical selected from the group consisting of the radicals of formula (a), (b), (c), (d) and (e):

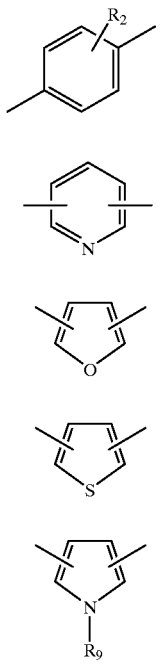

X represents —O—, —S(O)$_t$— or a radical —NR$_9$—,
Y and Z represent —O—, —S(O)$_t$— or a radical —CR$_{11}$R$_{12}$,
m is an integer equal to 1, 2 or 3,
n is an integer equal to 0 or 1,
p is an integer equal to 0, 1, 2 or 3,
t is an integer equal to 0, 1 or 2,
R$_3$, R$_5$, R$_9$, R$_{10}$, R$_{11}$ and R$_{12}$ represent, independently of each other, a hydrogen atom or a lower alkyl radical,
R$_4$ represents a lower alkyl radical,
R$_6$ represents a lower alkyl radical or a heterocycle,
R$_7$ represents a hydrogen atom, a lower alkyl radical or a radical:

wherein R' and R", which may be the same or different, represent a hydrogen atom, a lower alkyl radical, a mono- or polyhydroxyalkyl radical, an optionally substituted aryl radical or an amino acid or peptide or sugar residue, or, alternatively, taken together, form a heterocycle,
R$_8$ represents a hydrogen atom, a linear or branched alkyl radical containing from 1 to 20 carbon atoms, an alkenyl radical, a mono- or polyhydroxyalkyl radical, an optionally substituted aryl or aralkyl radical, a sugar residue or an amino acid or peptide residue,
wherein Y and Z cannot simultaneously represent an oxygen atom or a radical —S(O)$_t$—,
or a salt or chiral analogue of said compound.

2. The composition of claim 1, wherein at least one of the following is satisfied:
R$_1$ is a radical —CO—R$_7$
R$_2$ is a lower alkyl radical or a radical —OR$_9$,
Ar represents a radical of formula (a), and/or
X represents —O—, —S— or —NR$_9$—.

3. The composition of claim 1, wherein the compound of formula (I) is selected from the group consisting of
4-(5,6,7,8-Tetrahydro-5,5,8,8-tetramethyl-2-naphthyloxy)benzoic acid,
4-(5,6,7,8-Tetrahydro-5,5,8,8-tetramethyl-2-naphthylthio)benzoic acid,
4-(5,6,7,8-Tetrahydro-5,5,8,8-tetramethyl-2-naphthylsulfinyl)benzoic acid
4-(5,6,7,8-Tetrahydro-5,5,8,8-tetramethyl-2-naphthylsulfonyl)benzoic acid,
4-(5,6,7,8-Tetrahydro-5,5,8,8-tetramethyl-2-naphthylamino)benzoic acid,
5-(5,6,7,8-Tetrahydro-5,5,8,8-tetramethyl-2-naphthylthio)-2-thiophenecarboxylic acid,
4-(3,5,5,8,8-Pentamethyl-5,6,7,8-tetrahydro-2-naphthyloxy)benzoic acid,
4-(3,5,5,8,8-Pentamethyl-5,6,7,8-tetrahydro-2-naphthylthio)benzoic acid,
4-(3-Ethyl-5,5,8,8-tetramethyl-5,6,7,8-tetrahydro-2-naphthyloxy)benzoic acid,
4-(3-Isopropyl-5,5,8,8-tetramethyl-5,6,7,8-tetrahydro-2-naphthyloxy)benzoic acid,
4-(5,6,7,8-tetrahydro-5,5,8,8-tetramethyl-2-naphthyloxy)acetophenone,
4-(5,6,7,8-tetrahydro-5,5,8,8-tetramethyl-2-naphthyloxy)benzaldehyde,
4-(3-Bromo-5,6,7,8-tetrahydro-5,5,8,8-tetramethyl-2-naphthyloxy)benzoic acid,
3-Methyl-4-(5,6,7,8-tetrahydro-5,5,8,8-tetramethyl-2-naphthylthio)benzoic acid,
3-Methyl-4-(3,5,5,8,8-pentamethyl-5,6,7,8-tetrahydro-2-naphthylthio)benzoic acid,
3-Methyl-4-(3-ethyl-5,6,7,8-tetrahydro-5,5,8,8-tetramethyl-2-naphthyloxy)benzoic acid,
6-(3,5,5,8,8-Pentamethyl-5,6,7,8-tetrahydro-2-naphthylthio)nicotinic acid,
2-Hydroxy-4-(3,5,5,8,8-pentamethyl-5,6,7,8-tetrahydro-2-naphthylthio)benzoic acid,
2-Chloro-4-(3,5,5,8,8-pentamethyl-5,6,7,8-tetrahydro-2-naphthylthio)benzoic acid,
4-(3-Ethyl-5,6,7,8-tetrahydro-5,5,8,8-tetramethyl-2-naphthylthio)benzoic acid,
4-(3-Isopropyl-5,6,7,8-tetahydro-5,5,8,8-tetramethyl-2-naphthylthio)benzoic acid,
4-(3-n-Propyl-5,6,7,8-tetrahydro-5,5,8,8-tetramethyl-2-naphthylthio)benzoic acid,
4-(3,5,5,8,8-Pentamethyl-5,6,7,8-tetrahydro-2-naphthylthio)benzenemethanol,
4-(3,5,5,8,8-Pentamethyl-5,6,7,8-tetrahydro-2-naphthylthio)benzaldehyde,
N-Ethyl-4-(3,5,5,8,8-pentamethyl-5,6,7,8,-tetrahydro-2-naphthylthio)benzamide, and
N-4-Hydroxyphenyl-4-(3,5,5,8,8-pentamethyl-5,6,7,8-tetrahydro-2-naphthylthio)benzamide.

4. The composition of claim 3, wherein the compound of formula (I) is 4-(3,5,5,8,8-pentamethyl-5,6,7,8-tetrahydro-2-naphthylthio)benzoic acid.

5. The composition of claim 1, comprising from 0.0001% to 10% by weight of the compound of formula (I).

6. The composition of claim 5, comprising from 0.001 to 5% by weight of the compound of formula (I).

7. The composition of claim 6, comprising from 0.01 to 1% by weight of the compound of formula (I).

8. The composition of claim 1, wherein the lipophilic sunscreen is selected from the group consisting of p-aminobenzoic acid derivatives, salicylic acid derivatives, benzophenone derivatives, dibenzoylmethane derivatives, diphenylacrylate derivatives, benzofuran derivatives, polymeric UV screening agents containing one or more organosilicon residues, cinnamic acid esters, camphor derivatives, trianilino-s-triazine derivatives, phenylbenzimidazole-sulfonic acid and salts thereof, urocanic acid or the ethyl ester thereof, benzotriazoles, hydroxyphenyltriazine derivatives, bis(resorcinol)dialkylaminotriazines, and mixtures thereof.

9. The composition of claim 8, wherein the lipophilic sunscreen is selected from the group consisting of octyl salicylate, 3-benzophenone, butylmethoxydibenzoylmethane, octocrylene, octyl methoxycinnamate, and the compound of formula (II):

(II)

$$CH_3-Si(CH_3)_2-O-Si(CH_3)(CH_2CH(CH_3)Ar')-O-Si(CH_3)_3$$

[structure of compound (II): trisiloxane substituted with a 2-(2H-benzotriazol-2-yl)-4-methyl-6-propyl-phenol group]

10. The composition of claim 1, comprising from 0.001 to 30% by weight of the lipophilic sunscreen.

11. The composition of claim 1, further comprising at least one co-solubilizing agent selected from the group consisting of 2-alkyl-1-alkanols and esters thereof.

12. The composition of claim 11, wherein the co-solubilizing agent is selected from the group consisting of butyloctanol, hexyldecanol, octyldecanol, isostearyl alcohol, octyldodecanol, decyltetradecanol, undecylpentadecanol, dodecylhexadecanol, tetradecyloctadecanol, hexyldecyloctadecanol, tetradecyleicosanol, cetylarachidol, octyldodecyl octanoate, hexyldecyl caprylate, hexyldecyl laurate, hexyldecyl palmitate, hexyldecyl stearate and octyldodecyl meadowfoamate.

13. The composition of claim 1, further comprising at least one emulsifier selected from the group consisting of fatty acid esters of polyols.

14. A method of preparing the composition of claim 1, comprising combining the lipophilic sunscreen and the bicyclic aromatic compound.

15. A method of treating skin, comprising applying the composition of claim 1 to the skin.

16. A method of cosmetically treating skin, comprising applying the composition of claim 1 to the skin.

17. A method of treating skin acne, comprising applying the composition of claim 1 to skin afflicted with acne.

18. A method of treating chronological or actinic skin ageing, comprising applying the composition of claim 1 to the skin.

19. A method of treating the scalp, comprising applying the composition of claim 1 to the scalp.

20. A method of treating the greasy appearance of the hair and/or hair loss, comprising applying the composition of claim 1 to hair.

21. A method of dissolving a bicyclic aromatic compound represented by formula (I):

(I)

[structure of formula (I): bicyclic aromatic ring with substituents Y, Z, $R_2$, $R_1$, X—Ar]

wherein $R_1$ represents a hydrogen atom, a radical —$CH_3$, a radical —$CH_2$—O—$R_3$, a radical —$CH_2$—O—CO—$R_4$, a radical —O—$R_5$, a radical —O—$(CH_2)_m$—$(CO)_n$—$R_6$, a radical —CO—$R_7$, a radical —CO—O—$R_8$ or a radical —$S(O)_p$—$R_9$, $R_2$ represents a hydrogen atom or a halogen atom, a lower alkyl radical, an —$NO_2$ radical, a radical —O—$COR_4$, a radical —$OR_9$ or a radical:

[structure: —N($R_9$)($R_{10}$)]

Ar represents a radical selected from the group consisting of the radicals of formula (a), (b), (c), (d) and (e):

(a)

[structure (a): phenyl ring with $R_2$ substituent]

(b)

[structure (b): pyridyl ring]

(c)

[structure (c): furyl ring]

(d)

[structure (d): thienyl ring]

(e)

[structure (e): pyrrolyl ring with $R_9$ on N]

X represents —O—, —$S(O)_t$— or a radical —$NR_9$—,

Y and Z represent —O—, —$S(O)_t$— or a radical —$CR_{11}R_{12}$, m is an integer equal to 1, 2 or 3, n is an integer equal to 0 or 1, p is an integer equal to 0, 1, 2 or 3, t is an integer equal to 0, 1 or 2, $R_3$, $R_5$, $R_9$, $R_{10}$, $R_{11}$ and $R_{12}$ represent, independently of each other, a hydrogen atom or a lower alkyl radical, $R_4$ represents a lower alkyl radical, $R_6$ represents a lower alkyl radical or a heterocycle, $R_7$ represents a hydrogen atom, a lower alkyl radical or a radical:

wherein R' and R", which may be the same or different, represent a hydrogen atom, a lower alkyl radical, a mono- or polyhydroxyalkyl radical, an optionally substituted aryl radical or an amino acid or peptide or sugar residue, or, alternatively, taken together, form a heterocycle, $R_8$ represents a hydrogen atom, a linear or branched alkyl radical containing from 1 to 20 carbon atoms, an alkenyl radical, a mono- or polyhydroxyalkyl radical, an optionally substituted aryl or aralkyl radical, a sugar residue or an amino acid or peptide residue, wherein Y and Z cannot simultaneously represent an oxygen atom or a radical $—S(O)_t—$, or a salt or chiral analogue of said compound, comprising mixing the bicyclic aromatic compound with at least one lipophilic sunscreen.

* * * * *